United States Patent [19]

Hauze

[11] Patent Number: 4,798,292
[45] Date of Patent: Jan. 17, 1989

[54] STERILIZATION, STORAGE, AND PRESENTATION CONTAINER FOR SURGICAL INSTRUMENTS

[75] Inventor: Dennis R. Hauze, Bountiful, Utah

[73] Assignee: BioMedical Laser Industries, Houston, Tex.

[21] Appl. No.: 34,821

[22] Filed: Apr. 3, 1987

[51] Int. Cl.⁴ .............................................. B65D 81/18
[52] U.S. Cl. ..................... 206/439; 206/210; 206/363; 220/367; 422/300; 422/310
[58] Field of Search ............... 206/210, 363, 364–366, 206/370, 438, 439, 558, 561; 220/366–373, 22.3, 74, DIG. 6, 4 E; 422/300, 310, 276

[56] References Cited

U.S. PATENT DOCUMENTS

| | | | |
|---|---|---|---|
| 2,384,398 | 9/1945 | Raven . | |
| 2,786,245 | 3/1957 | Steinboch, Jr. | 422/310 |
| 2,798,784 | 7/1957 | Marshall | 220/4 E |
| 3,417,894 | 12/1968 | Gittler | 220/4 E |
| 3,656,650 | 4/1972 | Frater | 220/22.3 |
| 3,723,061 | 3/1973 | Stahl | 206/370 X |
| 4,105,407 | 8/1978 | Sanderson . | |
| 4,149,650 | 4/1979 | Whelchel et al. | 220/231 |
| 4,247,517 | 1/1981 | Sanderson et al. . | |
| 4,262,799 | 4/1981 | Perrett | 206/363 |
| 4,372,921 | 2/1983 | Sanderson et al. . | |
| 4,418,829 | 12/1983 | Clay | 220/74 |
| 4,466,552 | 8/1984 | Butterworth et al. . | |
| 4,478,349 | 10/1984 | Haverland, Jr. et al. | 220/366 X |
| 4,485,919 | 12/1984 | Sandel | 206/370 |
| 4,512,498 | 4/1985 | Leibinger | 220/371 |
| 4,551,311 | 11/1985 | Lorenz | 422/300 |
| 4,562,047 | 12/1985 | Sestak et al. | 422/300 |
| 4,576,309 | 3/1986 | Tzlfkansky et al. | 220/366 |
| 4,617,178 | 10/1986 | Nichols | 422/310 |
| 4,661,326 | 4/1987 | Schainholz | 422/310 |
| 4,671,943 | 6/1987 | Wahlquist | 422/300 |

FOREIGN PATENT DOCUMENTS 2207339 9/1973 Fed. Rep. of Germany .
2375869 7/1978 France .

OTHER PUBLICATIONS

AMSCO Eagle Steriset Technical Report, 1983.
Product Literature from Martin U.S.A., 1984.
Product Literature from Genesis Medical Corporation.
Product Literature from American Container Techology (ACT).
Product Literature of AESCULAP Instruments Corporation.
Product Literature from Instru Med., Inc.,

*Primary Examiner*—Stephen Marcus
*Assistant Examiner*—Bryon Gehman
*Attorney, Agent, or Firm*—J. Winslow Young

[57] ABSTRACT

A sterilization, storage, and presentation container, the container including a tray and a cover which can be inverted to form a second tray. Instrument support means are provided through insert boards, dividers, clip retainers and open-cell, synthetic foam devices. The insert boards include holes for the passage of the sterilizing medium and the holes in the lower insert board can receive pegs to further support the instruments.

23 Claims, 5 Drawing Sheets

U.S. Patent  Jan. 17, 1989  Sheet 5 of 5  4,798,292
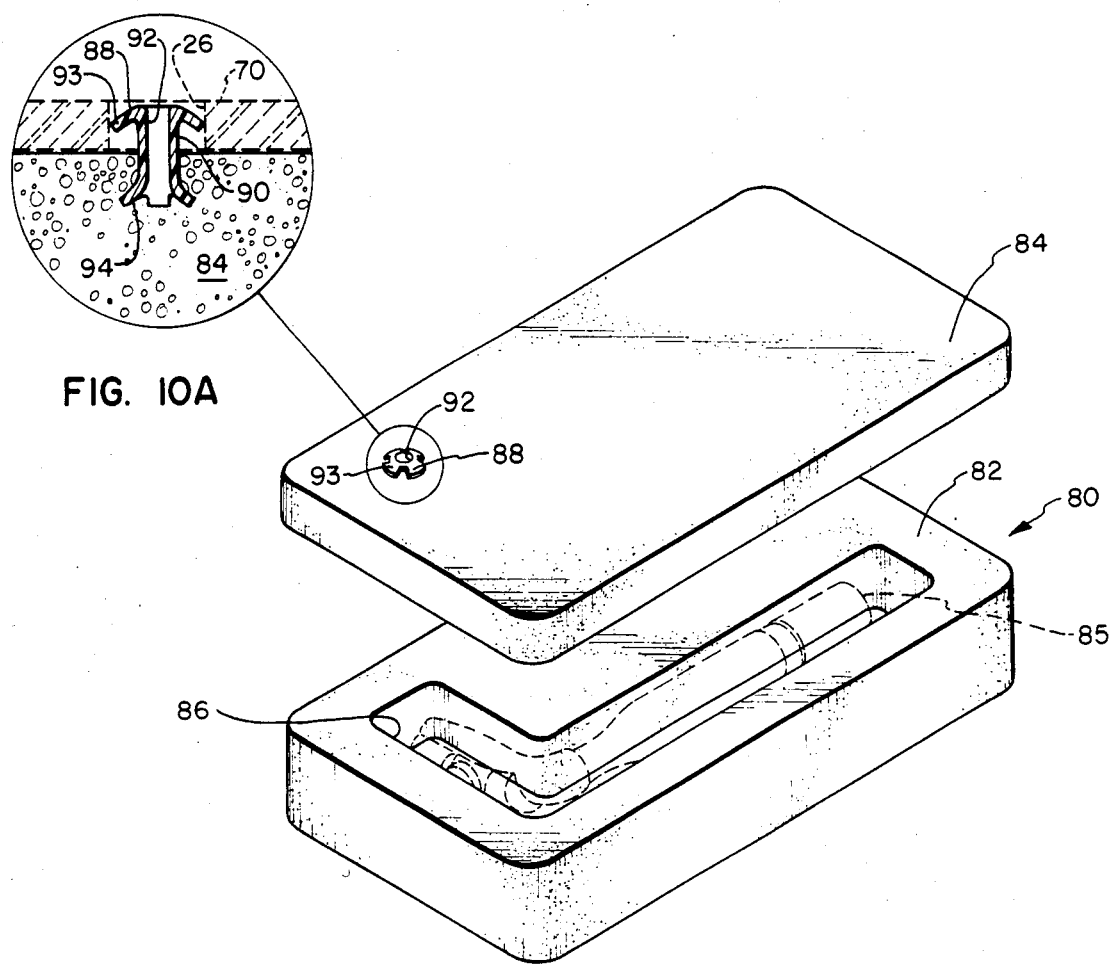
FIG. 10A
FIG. 10
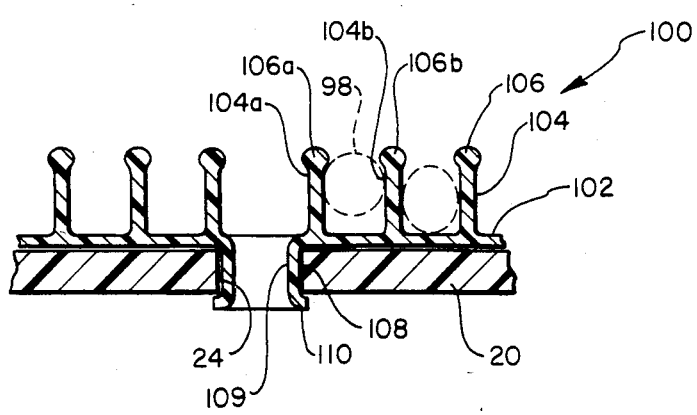
FIG. 11

STERILIZATION, STORAGE, AND PRESENTATION CONTAINER FOR SURGICAL INSTRUMENTS

CROSS-REFERENCE TO RELATED APPLICATION

A container for surgical instruments and materials in combination with a wrap system to provide a sterile environment for said surgical instruments and materials is described and claimed in copending application Ser. No. 07/034308, now abandoned, entitled Surgical Instrument Container AND Wrap System, filed on even date in the name of Dennis R. Hauze.

BACKGROUND OF THE INVENTION

1. Technical Field

The present invention relates to an improved container for sterilization, storage, and presentation of surgical instruments and materials, and, more particularly, to a sterilization, storage, and presentation container which includes removable insert boards and retainer systems to which the surgical instruments and materials are releasably mounted. Dividers and synthetic foam systems, as well as pegs and clip retainers, removably secured to the insert boards, provide the mounting system for the surgical instruments and materials. The container of the present invention is especially well-suited for use with a sterilization wrap.

2. Background Information

Surgery involves highly complex procedures which are accomplished with a significant number of specialized instruments and devices. Any instrument or device used by the surgeon during a surgical procedure must be readily available and presented in an orderly, readily accessible manner. It is clearly understood, of course, that such instruments and devices also must be presented in a sterile condition. Presentation is next in importance to sterility, since many surgical procedures require prompt access to certain instruments, the absence of which could result in serious injury, or even death, to the patient.

It is customary to provide the appropriate types and quantities of surgical instruments and materials for a specific surgical procedure as a unitary package that previously has been sterilized and maintained in a sterile condition by reason of the packaging system employed. Such sterilization and maintenance in general are accomplished by one of three methods, described below.

The earliest and most simple method for sterilizing surgical instruments and materials, which still is used to a limited extent today, involves directly wrapping the articles in at least one sheet of a porous material, such as paper, a towel, muslin, or a disposable, nonwoven fabric, sealing the wrapped package with tape, and placing the package in a sterilizing autoclave. Sterilizing medium enters the autoclave chamber and penetrates the porous material of the package to contact the articles contained within. Some autoclaves provide for the removal of air before introduction of the sterilization medium and/or the removal of moisture after autoclaving by means of a vacuum-drying cycle. With most of such autoclaves, atmospheric pressure is restored within the autoclaves by admitting room air prior to removal of the package placed therein.

While relatively simple, the above method did not make the surgical instruments and materials readily accessible in an orderly manner. Unless multiple layers of wrapping were employed, contamination by microorganisms or particles of wrapping was a frequent occurrence. Furthermore, the shelf life of the sterilized package was relatively short, necessitating resterilization prior to use. Another consequence commonly resulting from the use of the above method was the loss of or damage to expensive instruments. Frequently, the wrapping is spread out on a table in an operating room and the instruments are placed thereon after use. Subsequently, the wrapping is gathered up and disposed of, or set aside for reuse. Unless the instruments are meticulosly removed from the wrapping, they can be lost or damaged.

In order to obviate some of the disadvantages associated with the foregoing method, the surgical instruments and materials were placed in open trays, with or without lids. The trays then were wrapped and sterilized, as with the first method. The advantage to this method is that the instruments can be organized for presentation, and the tray provides a receptacle for the collection of used instruments. See, by way of illustration only, U.S. Pat. No. 2,384,398, which describes a sterilization container. The container consists primarily of an outer casing and an inner basket, with the basket being placed in a porous bag which provides the barrier against microorganisms upon the completion of sterilization.

A variation of the foregoing is described in U.S. Pat. No. 4,466,552, which describes a sterilization container formed of a nonwoven material. In this case, however, the nonwoven material has been treated with a resin, thereby giving the container sufficient rigidity to permit its use in the same way as a metal or plastic container. The nonwoven material remains porous, thereby facilitating sterilization, but still serves as a barrier against microorganisms.

More recently, rigid containers have been developed which do not require an external sterilization wrap. Examples of such containers are found in the reference described below.

German Patent Application No. P 22 07 339.8-41, published as No. 2 207 339, describes a surgical instrument container closed by a lid and having a perforated bottom which can be covered by a filter. The container has an intermediate frame forming the sidewalls and the perforated bottom is releasably connected to this frame. A support frame inside the intermediate frame extends over the opening left when the bottom is removed.

A variation of the above-described container is found in French Pat. No. 2,375,869. Either or both of the base and cover of the described sterilization container can be perforated and covered on their inside face with a fabric or paper filter, held in place by the convex side of a perforated pressure plate of slightly cylindrical curvature against such inside face.

U.S. Pat. No. 4,105,407, describes a sterilizing container having a lid with an outer flange which cooperates with the upper edge of a base and a resilient member for sealing the container. The lid contains a mechanism for automatically moving the lid into sealing engagement with the base. The container is designed to receive articles such as medical instruments which are sterilized when the container is placed in an autoclave, subjecting the instruments or articles to a sterilizing environment. The moving mechanism on the lid includes a means responsive to the sterilizing environment to automatically bring the lid into sealing contact with the base prior to the return of the surrounding environment to ambient conditions, thereby preserving the instruments in a sterile condition until needed for use. Variations of this container are described in U.S. Pat. Nos. 4,247,517 and 4,372,921. Moreover, containers embodying one or more of the features described in the foregoing references are available commercially from such companies as American Container Technology, Inc., Wallington, N.J. 07057; Aesculap Instruments Corporation, Burlingame, Calif. 94010; InstruMed, Inc., Kirkland, Wash. 90834; American Sterilizer Company, Erie, Pa. 16506; Martin U.S.A., Inc., Stamford, Conn. 06902; and Genesis Medical Corporation, Cleveland, Ohio 44130.

The open trays and rigid containers described above range from relatively simple devices, such as a closed container, having apertures therein or a sieve placed in the bottom on the container for entry of a sterilizing agent, to complex devices, such as containers provided with elaborate mechanisms for closing the cover of the device after a sterilizing gas has had sufficient time to enter the container. Other containers, intermediate in complexity between the aforementioned devices, are those sterilization containers having apertures passing from an outer surface to an inner surface of the container and provided with a porous material covering one of the apertured surfaces. The porous material is selected to permit passage of air and other gases, but to be impervious to the passage of microorganisms. All of such devices are intended to provide ingress and egress of air or a sterilizing gas during the sterilization procedure, but to exclude contaminants during and subsequent to the sterilization procedure.

As already noted, presentation is important since it displays the various instruments in a readily accessible format. Further, it is critical that certain types of surgical instruments and devices such as prosthetics are adequately protected during sterilization, storage, and handling, as well as being readily available during presentation.

SUMMARY OF THE INVENTION

The present invention has as its principle object to provide a combination sterilization, storage, and presentation container for surgical instruments and materials which can be readily assembled to receive any suitable type and quantity of surgical instruments and materials in any of a number of preselected arrangements.

A further object is to provide such a container having a transparent, removable cover to allow trained personnel to see the instruments inside prior to opening the container.

A further object is to provide a plurality of devices and structures for placement inside the combination sterilization, storage, and presentation container for retaining the surgical instruments and materials to assist in accomplishing the functions of sterilization, storage, and presentation of the surgical instruments and materials.

Another object is to provide a removable insert for such a container, the removable insert having a plurality of peg-receiving apertures with pegs removably secured in a preselected number of apertures in a preselected pattern to releasably support the surgical instruments on the insert.

Accordingly, the present invention provides a container for the sterilization and storage of surgical instruments and materials and for the subsequent presentation of said surgical instruments and materials during a surgical procedure, which container comprises:

a tray comprising a bottom with spaced, permanent apertures, a peripheral shelf around the bottom, surrounding sidewalls, and a marginal flange around the upper periphery of said sidewalls;

a cover removably mounted on said tray and defining an interior chamber therewith, said cover being carried on said marginal flange of said tray and having a plurality of spaced, permanent apertures; and, a removable instrument support means comprising permanent aperture means for admitting a sterilizing medium into intimate contact with said surgical instruments and materials and support means for releasably supporting said surgical instruments and materials in a readily accessible manner.

The present invention also provides a container for the sterilization and storage of surgical instruments and materials and for the subsequent presentation of said surgical instruments and materials during a surgical procedure, which container comprises:

a first tray comprising a bottom with spaced, permanent apertures; a raised lower shelf surrounding said bottom; raised sidewalls; and an upper, raised shelf on the upper edge of said sidewalls, said raised shelf being formed as a marginal flange;

a cover comprising a second tray adapted to be removably mounted on said first tray and defining an interior chamber therewith, said cover being carried on said marginal flange of said first tray and having a plurality of spaced, permanent apertures and forming said second tray when inverted; and first and second removable support means for said surgical instruments and materials.

The container of the present invention is intended for use with a sterilization wrap.

BRIEF DESCRIPTION OF THE DRAWINGS

FIG. 10 is a perspective view of a synthetic foam insert, while 10a is an enlarged, cross-sectional view of a fragmentary portion of FIG. 10.

FIG. 11 is a fragmentary, cross-sectional view of a retainer clip system for this invention.

DETAILED DESCRIPTION OF THE INVENTION

The present invention is best understood by reference to the following detailed description with reference to the accompanying drawings wherein like parts are designated with like numerals throughout.

Figure 1:
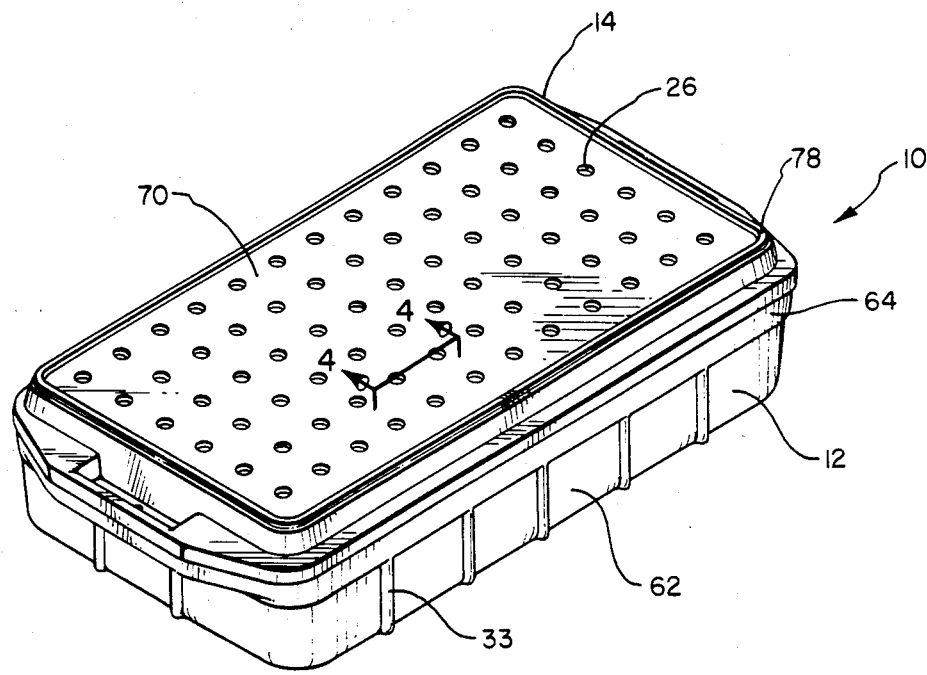
FIG. 1 is a perspective view of the novel container system of this invention.
Figure 2:
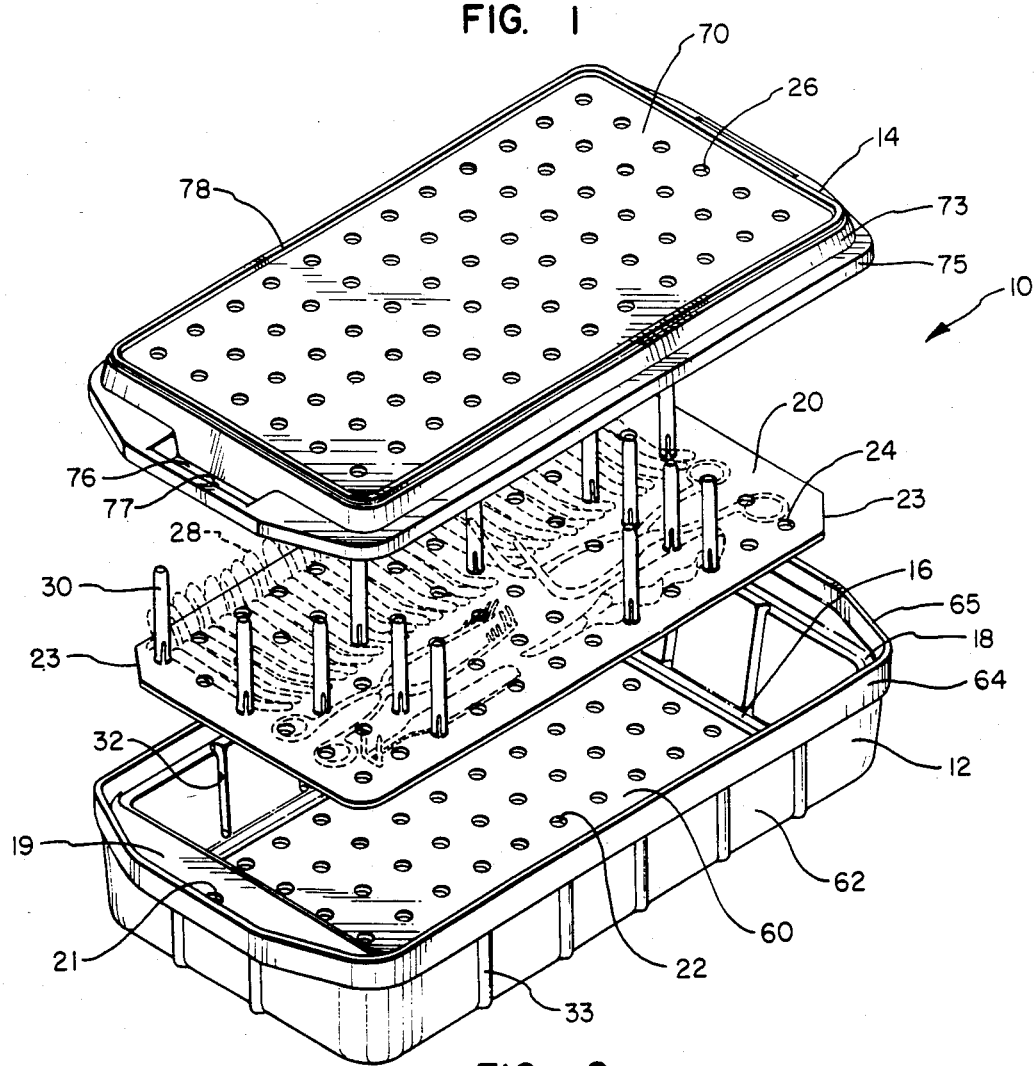
FIG. 2 is an exploded, perspective view of the novel container system shown in FIG. 1 showing a first embodiment of an insert.

Referring now to FIGS. 1 and 2, a first preferred embodiment of the sterilization, storage and presentation container of this invention is shown at 10. Container 10 includes a tray 12, a matching cover 14 and an insert 20. Tray 12 is shown as having a generally rectangular configuration although it may have any general configuration, i.e., with a round, elliptical, square, or other suitable configuration, although the illustrated, rectangular configuration is presently preferred. Tray 12 is formed as a unitary piece having a base 60 with a plurality of permanent apertures or holes 22 therethrough and surrounding sidewalls 62. Slots 32 face inwardly and create outwardly protruding ribs 33 in sidewalls 62. The function of holes 22 and slots 32 will be described more fully hereinafter.

The lower edges of sidewalls 62 terminate in a lower shelf 16 raised an incremental distance above tray base 60 while the upper edges of sidewalls 62 include an upper shelf 18 with a surrounding, raised margin 64 having a rim 65. Upper shelf 18 at each end of tray 12 extends outwardly in the presently preferred embodiment to form handles 19, each having a hole 21 therethrough.

Figure 3:
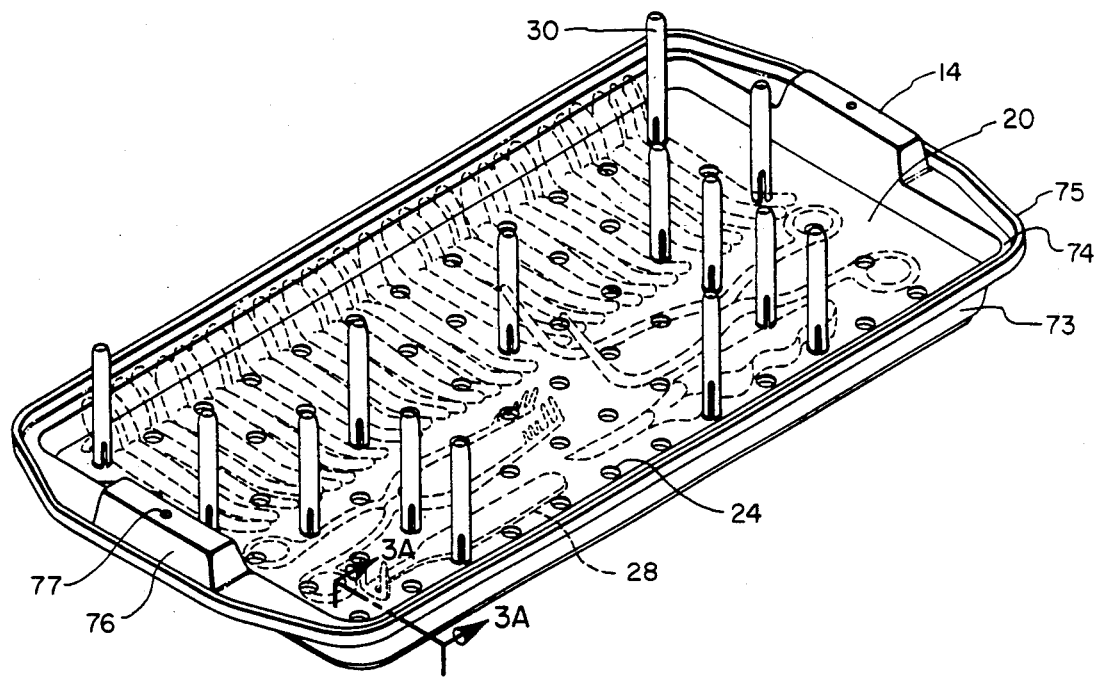
FIG. 3 is a perspective view of the cover for the container of FIGS. 1 and 2 shown inverted with the insert of FIG. 2 placed therein.
Figure 3A:
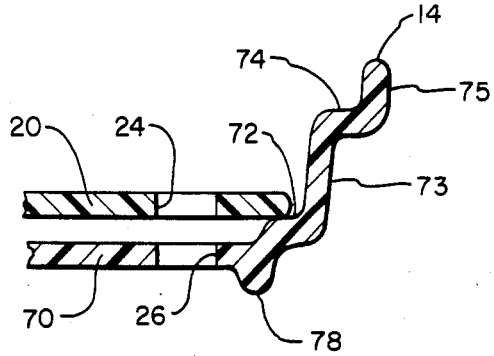
FIG. 3A is a fragmentary, cross-sectional view taken along lines 3a-3a of FIG. 3.

Cover 14 is fabricated from a transparent plastic material to allow visual observation of the underlying surgical instruments and materials. Cover 14 includes a planar surface or deck 70 having a plurality of spaced, permanent apertures or holes therethrough. An internal shelf 72 (FIG. 3A) surrounds deck 70 and is raised an incremental distance above deck 70. A ridge 78 around the external periphery of deck 70 provides a pedestal upon which cover 14 rests when cover 14 is inverted to form a tray for insert 20 as shown in FIGS. 3 and 3A. The periphery of cover 14 includes a raised margin 73 having a seat 74 and a lip 75. Seat 74 rests against rim 65 on the upper edge of margin 64 of tray 12 to form a sealing relationship between cover 14 and tray 12.

A depression 76 is formed in a portion of the seat 74 as an extension thereof and dimensionally corresponds to the configuration of handle 19 on tray 12 with a hole 77 therein in registry with hole 21 in handle 19. Hole 77 in depression 76 in combination with hole 21 in handle 19 forms a condensate escape route for any moisture that may collect in depression 76 during the steam sterilization process. Further, a security band (not shown) may be passed through holes 77 and 21 to secure cover 14 to tray 12 and to provide an indication if the internal integrity of container 10 has been breached.

Insert 20 is fabricated from a planar material having sufficient rigidity or internal strength to support thereon a plurality of surgical instruments 28 (shown in broken lines to illustrate the overall environment of insert 20). Instruments 28 may be any preselected number and variety of surgical instruments and materials suitable for the intended surgical procedure. A plurality of pegs 30 are inserted in holes 24 in a preselected configuration so as to provide a desired degree of support to instruments 28 to keep them in alignment on insert 20 and to reduce damage of the same through the normal handling procedures of container 10. Pegs 30 also are useful in keeping instruments 28 from sliding off insert 20 during transfer of insert 20 from tray 12 to the tray formed when cover 14 is inverted as shown in FIG. 3. Removal of insert 20 from tray 12 is facilitated by cutouts 23 on opposite corners of insert 20.

Figure 4:
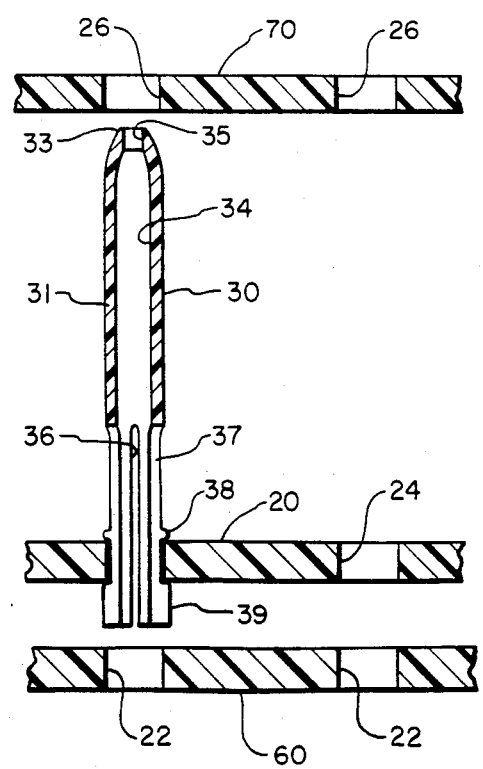
FIG. 4 is a fragmentary, cross-sectional view taken along lines 4—4 of FIG. 1.
Figure 5:
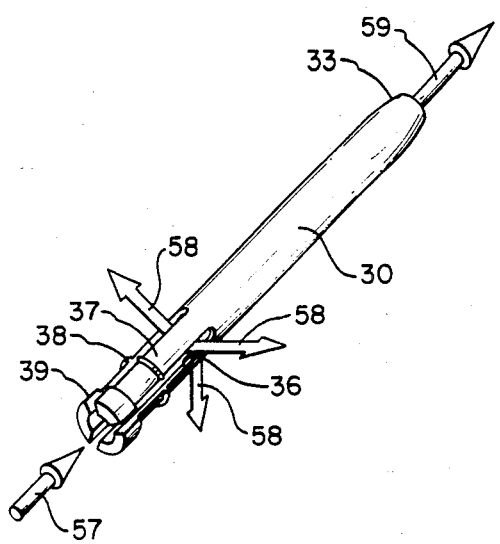
FIG. 5 is a perspective view of a hollow peg showing the flow of sterilizing medium therethrough.

Referring particularly to FIGS. 4 and 5, the function of peg 30 and the relationship between peg 30 and the other adjacent elements of container 10, more particularly, base 60 and deck 70 as well as insert 20 is more clearly illustrated in FIG. 4. Peg 30 is fabricated as a hollow tube 31 having a tip 33 with a port 35 therein. The lower end of hollow tube 31 is formed into a plurality of legs 37 with slots 36 therebetween. Peg 30 includes a detent 38 formed as a raised ring around legs 37 and an enlarged base or stop 39 on the bottom end. Peg 30 is dimensionally configured to be inserted into hole 24 in insert 20 with detent 38 resting against the upper surface of insert 20 and with stop 39 against the bottom surface of insert 20.

Peg 30 is mounted to insert 20 by passing tip 33 upwardly through hole 24 until detent 38 contacts the bottom surface of insert 20. Pegs 30 are fabricated from a suitably resilient material such as a plastic so that legs 37 are flexed inwardly to allow detent 38 to pass upwardly through hole 24 at which time legs 37 snap outwardly to a position essentially approximating the internal diameter of hole 24. The dimensions of peg 30 are such that peg 30 is not tightly constricted in hole 24 but has sufficient gap distance to allow peg 30 to flex laterally under side forces when instruments 28, for example, shift during handling. Otherwise, pegs 30 would tend to be easily snapped off under such side forces.

Stop 39 engages the bottom surface of insert 20 and prevents peg 30 from being pulled upwardly out of hole 24. This latter feature is important since it prevents peg 30 from becoming a loose item which could accidentally fall into the surgical site and be lost inside the incision. This latter event could be catastrophic, particularly since peg 30 is not customarily fabricated from a radiopaque material which can be observed through conventional X-ray equipment.

Peg 30 is hollow, not only to provide the necessary flexibility to legs 37, but to also allow the passage of steam illustrated schematically at arrows 57, 58 and 59 (FIG. 5). Entering steam, arrow 57, passes outwardly through slots 36 as arrows 58, while the balance, arrow 59, passes through port 35. Steam 58 contacts adjacent surgical instruments 28 (FIG. 2) to provide improved sterilization.

Figure 6:
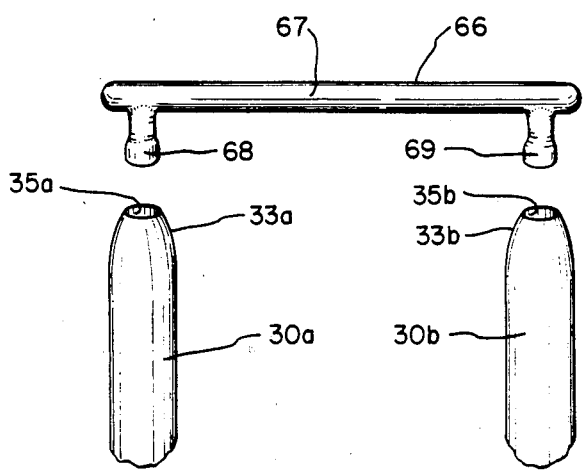
FIG. 6 is a fragmentary, perspective view of a retainer system involving at least two pegs.

With particular reference to FIG. 6, a retainer 66 is shown in juxtaposition with pegs 30a and 30b. Retainer 66 is fabricated from a plastic, rubber, or other suitable material and is designed to releasably engage the tips 33a and 33b of pegs 30a and 30b, respectively, to serve as a retainer for instruments 28 (FIGS. 2 and 3) between pegs 30a and 30b. Retainer 66 includes a body 67 and a pair of downwardly extending nipples 68 and 69 which are dimensionally configured to be releasably engaged in ports 35a and 35b, respectively. In this manner, retainer 66 serves as the retainer previously described. Body 67 can be of any suitable configuration or dimension to provide the desired retention capability to retainer 66. For example, body 67 can be configured with a downwardly extending, relatively rigid tab (not shown) which would press downwardly against instruments 28 (FIGS. 2 and 3).

Figure 7:
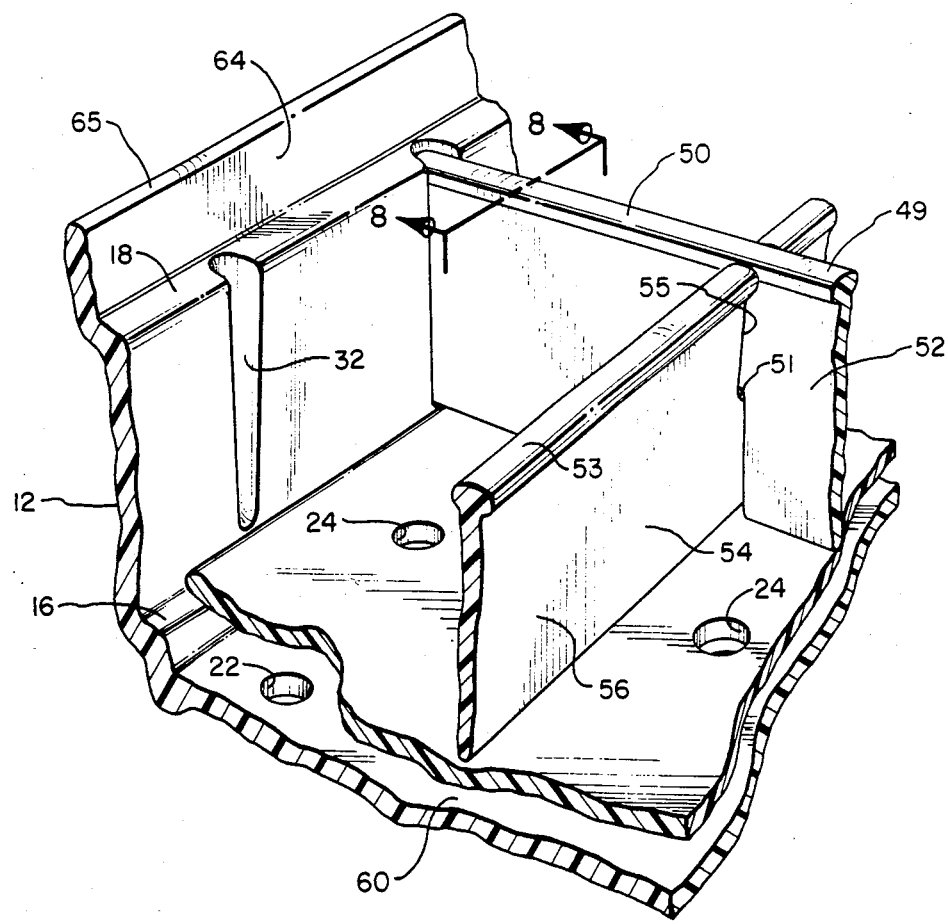
FIG. 7 is a fragmentary, perspective view of a divider system for the tray.
Figure 8:
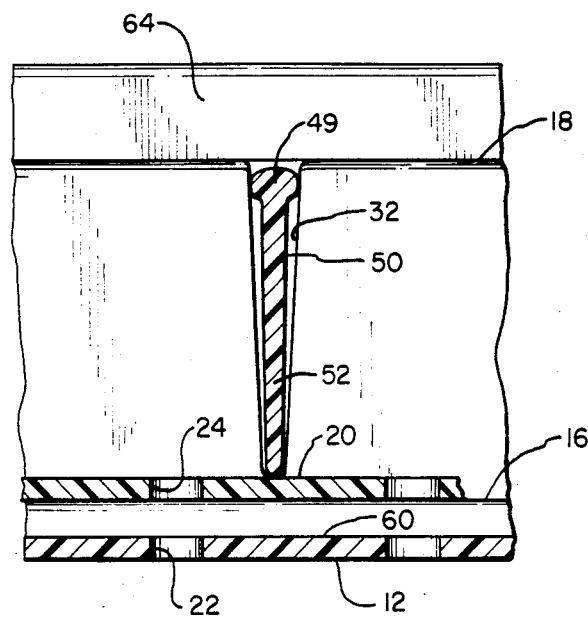
FIG. 8 is a cross-sectional view taken along lines 8—8 of FIG. 7.

Referring now to FIGS. 7 and 8, a divider system is shown for tray 12 and includes a lateral divider 50 in cooperation with a longitudinal divider 54 intersecting and interlocking therewith. Lateral divider 50 includes a web 52 with a rib 49 formed along the upper edge. The end of web 52 is easily received in the tapered configuration of slot 32, while the sides of rib 49 securely engage the sidewalls of slot 32 to releasably interlock lateral divider 50 in slot 32. The upper surface of rib 49 rests incrementally below upper shelf 18 so as to provide clearance to an insert (not shown) placed thereon. A notch 51 is cut in web 52 and is designed to engage a portion of a web 56 of a corresponding divider 54. Divider 54 also includes a rib 53 and a downwardly cut notch 55 so as to interlock divider 54 with lateral divider 50 as shown. Ribs 49 and 53 impart a desirable degree of longitudinal stability to the respective dividers as well as serving to interlock the same into the relevant slot 32.

Figure 9:
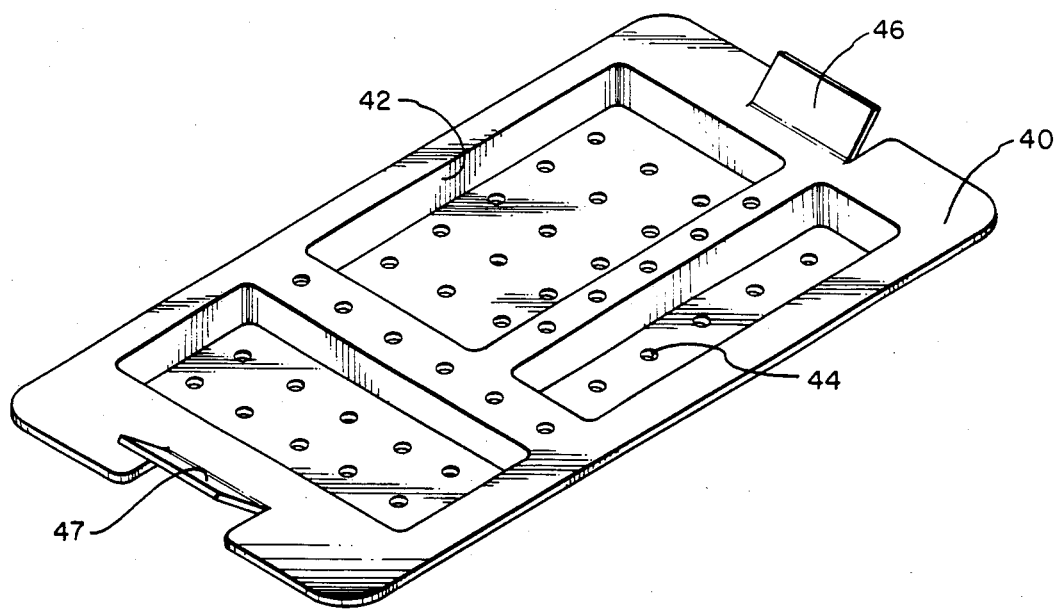
FIG. 9 is a perspective view of an upper insert embodiment for this invention.

Referring specifically to FIG. 9, a second or upper insert 40 is shown and may include a plurality of basins 42 molded therein. Upper insert 40 is configured to rest on upper insert shelf 18 with basins 42 extending downwardly into the interior of tray 12. Upper insert 40 includes a plurality of permanent apertures or holes 44 therein which allow the passage therethrough of the particular sterilizing medium such as steam, or the like. The number, shape, and depth of basins 42 may be selectively predetermined so as to receive the particular surgical instruments and/or materials (not shown). For example, in one presently preferred embodiment, container 10 is configured for a surgical procedure in the field of orthopedic implantation. Upper insert 40 is designed to hold the surgical instruments necessary for carrying out the surgical procedure, while insert 20 supports a plurality of size range of the type of implant for trial or implant during the surgical procedure. This method of presentation is advantageous in that it allows the surgeon (not shown) to select the appropriate size of implant from the range of sizes presented.

Referring particularly to FIG. 10, a foam insert is shown generally at 80 and includes a basal element 82 and an overlay 84, both of which are fabricated from an open-cell, foam material such as polyurethane foam. Such foams are commercially available and are used in numerous applications, particularly for cushioning delicate instruments against shock damage. The open cell construction allows the sterilizing gaseous medium to penetrate the body of basal element 82 and overlay 84 into intimate contact with any surgical instruments or materials supported therein, in this instance a surgical device illustrated schematically by broken lines at 85 and nested in a cavity 86.

A plurality of cavities 86 may be provided in basal element 85 and be preshaped in any desirable configuration to receive, protect, and present the desired surgical instrument 85. The thickness of basal element 82 is selectively predetermined to provide the appropriate depth to cavity 86 while retaining a desirable degree of bottom thickness at the bottom of a cavity 86. Basal element 82 is designed to rest on insert 20, although it may be inserted directly into tray 12 so as to rest directly against base 60. The dimensions of basal element 82 are selectively coordinated with the internal dimensions of tray 12 so as to be snugly received therein to preclude dislodgment of basal element 82 when instrument 85 is removed from cavity 86.

Overlay 84 can be secured inside cover 14 (FIGS. 1–3) and for this purpose can include a plurality of retainers 88 (only one of which is shown herein for ease of illustration) to releasably secure overlay 84 to the interior of cover 14. Referring particularly to FIG. 10A, retainer 88 is shown in the environment of deck 70 of cover 14 and is releasably lodged in a hole 26. Retainer 88 is fabricated from a tubular element such as a length of plastic tubing 90 having a hollow throughbore 92 with outwardly extending upper fingers 93 at the upper end and outwardly extending lower fingers 94 at the lower end. Retainer 88 is pressed downwardly into the upper surface of overlay 84, causing lower fingers 94 to engage the foam material of overlay 84. Sufficient length of retainer 88 is left protruding above overlay 84 to allow retainer 88 to be inserted upwardly into hole 26 in deck 70 with upper fingers 93 in frictional engagement with the internal walls of hole 26. In this manner, overlay 84 is releasably engaged to the inner surface of cover 14 so that when cover 14 is lifted from tray 12, overlay 84 also is removed and instrument 85 is presented.

Referring specifically to FIG. 11, a small instrument retainer is shown generally at 100 and includes a retainer base 102, having a plurality of clip fingers 104 extending upwardly therefrom. The upper ends of clip fingers 104 are enlarged to form enlargements 106. Instrument retainer 100 is fabricated from a suitable, resilient material such as rubber and is designed to be releasably engaged to insert 20 (FIGS. 1–3), where it serves as a retainer for releasably securing a plurality of small instruments (shown herein with dashed lines as instruments 98). Clip fingers 104 may be either discrete elements having a uniform circular cross section or may be fabricated as longitudinal elements. In either embodiment, the function is identical so as to protect and releasably secure small instruments 98 against loss or damage while holding them readily accessible for presentation as described hereinbefore. Instrument retainer 100 is generally configured to cover only a portion of insert 20 or upper insert 40, although any suitable size may be used in conjunction with the particular insert.

A hollow, raised boss 108 is formed in retainer base 102 and has an enlarged retention ring 110 on the end. The length of raised boss 108 corresponds to the thickness of insert 20 so that raised boss 108 can be inserted through hole 24, allowing retention ring 110 to snap outwardly to releasably engage the bottom surface of insert 20. Hollow throughbore 109 is raised boss 108 allows the passage of sterilizing medium to thoroughly sterilize instruments 98 and the other contents of container 10 (FIGS. 1 and 2).

Sterilization involves the destruction of all microorganisms within the sterilization zone. Clearly, it is essential that all portions of the sterilization zone be readily accessible to the particular sterilizing medium, whether it is heat, steam, gases, or a combination thereof. Container 10 and the various components thereof are advantageously suitable for this purpose by reason of the configuration of the various elements. For example, holes 22, 24, and 26 in each of tray base 60, insert 20, and lid deck 70, respectively, are in general alignment or registry to facilitate the rapid passage of the particular sterilizing medium such as steam 57–59 (FIG. 5).

The open structure by which instruments 28 (FIG. 3) and 85 (FIG. 10) are supported in container 10 advantageously exposes each of them and their surroundings to complete contact with the sterilizing agent. Not only is it important that the sterilizing agent be introduced efficiently into container 10, but it must also be removed efficiently to eliminate exposure of personnel to the same when container 10 is removed from the sterilizing environment. Accessibility is readily provided throughout container 10 by the configuration and structural relationship of the various components.

The rigid components of container 10, tray 12, cover 14, inserts 20 and 40, pegs 30, as well as dividers 50 and 54, are fabricated from a suitable, heat resistant and sterilizable material such as polysulfone. The remaining materials of construction are obtained from the material having the desired structural characteristics such as flexibility, resilience, and, in the case of foam insert 80, the necessary open-cell construction to allow passage of the sterilizing medium. All these materials are commercially available.

Container 10 is, therefore, a versatile, economical, and convenient system for sterilization, storage, and presentation of the particular surgical instruments and materials contained therein, in this case, instruments 28 (FIGS. 2 and 3) and instrument 85 (FIG. 10). As previously discussed in brief, it is important that such surgical instruments be stored after sterilization in a secure environment in a protected condition. Presentation is another important feature since instrument accessibility is crucial both for patient safety as well as providing significant savings in time for the surgeon and the duration of occupancy of the surgical suite.

The novel advantages of container 10 are particularly enhanced when coupled with the newer wrap systems specifically prepared to meet the rigorous demands of the medical profession. Excellent examples of fabrics having the desirable characteristics for sterilization wrap materials are commercially available from Kimberly-Clark Corporation, Roswell, Georgia, under their trademarks "KIMGUARD" and "SPUNGUARD". Both of these materials are available in a variety of weights and bonding characteristics to meet these exacting demands.

The present invention may be embodied in other specific forms without departing from its spirit or essential characteristics. The described embodiments are to be considered, in all respects, only as illustrative and not restrictive. The scope of the invention is, therefore, indicated by the appended claims rather than by the foregoing description. All changes which come within the meaning and range of equivalency of the claims are to be embraced within their scope.

I claim:

1. A container for the sterilization and storage of surgical instruments and materials and for the subsequent presentation of said surgical instruments and materials during a surgical procedure, which container comprises:

a tray comprising a bottom with spaced, permanent apertures, a peripheral shelf around the bottom, surrounding sidewalls, and a marginal flange around the upper periphery of said sidewalls;

a cover removably mounted on said tray and defining an interior chamber therewith, said cover being carried on said marginal flange of said tray and having a plurality of spaced, permanent apertures;

a removable insert board having a plurality of spaced, permanent apertures for admitting a sterilizing medium into intimate contact with said surgical instruments and materials;

and support means on said insert board for releasably supporting said surgical instruments and materials in a readily accessible manner comprising pegs configured a hollow tubes for the passage of sterilizing medium, each peg having an upper end and a bottom end, said bottom end terminating in a stop and having longitudinal slots extending an incremental distance toward said upper end, said slots forming legs in said hollow tube, said pegs being adapted to being inserted upwardly through said spaced apertures until said stop engages the bottom surface of said insert board with said legs providing a resilient engagement of said pegs in said apertures.

2. The container defined in claim 1 wherein said tray includes raised side walls with handles formed as outwardly extending projections from said side walls.

3. The container defined in claim 2 wherein said handles are formed as extensions of said marginal flange.

4. The container defined in claim 3 wherein said extensions include a bottom surface with a rim around the periphery of the bottom surface.

5. The container defined in claim 4 wherein said bottom surface includes an aperture for drainage.

6. The container defined in claim 2 wherein said cover includes outwardly extending projections which form handles for said cover.

7. The container defined in claim 6 wherein said handles correspond to said handles on said tray and include at least one hole in each of said handles with said holes being in registry and adapted to receive a banding means for securing said container cover to said tray.

8. The container defined in claim 1 wherein said insert board includes means for removing said insert board from said tray and said container cover.

9. The container defined in claim 1 wherein said container comprises a second insert board and means for aligning said second insert board in said tray in spaced relationship to said insert board, said second insert board including a plurality of holes therethrough.

10. The container defined in claim 1 wherein said pegs include a raised, circumferential ridge for releasably interlocking said pegs in said spaced apertures by resting against the upper surface of said insert board while said stop is in engagement with said bottom surface, said pegs further comprising a retainer for releasably engaging the upper end of said pegs and comprising a body extending between said pegs and having downwardly extending nipples dimensionally configured to be releasably engaged in said upper ends of said hollow tubes of said pegs.

11. The container defined in claim 10 wherein said longitudinal slots in said pegs extend beyond said circumferential ridge so as to provide slot openings above said upper surface of said insert boards to allow sterilizing medium to pass outwardly through said slot openings.

12. The container defined in claim 1 including a second, insert board adapted to be removably received in an upper portion of said tray, said second insert board comprising a plurality of permanent apertures therethrough and at least one depression formed therein for receiving a surgical instrument.

13. A container for the sterilization and storage of surgical instruments and materials and for the subsequent presentation of said surgical instruments and materials during a surgical procedure, which container comprises:

a first tray comprising a bottom with spaced, permanent apertures; a raised lower shelf surrounding said bottom; raised sidewalls; and an upper, raised shelf on the upper edge of said sidewalls, said raised shelf being formed as a marginal flange;

a cover adapted to be removably mounted on said first tray and defining an interior chamber therewith, said cover being carried on said marginal flange of said first tray and having a plurality of spaced, permanent apertures and forming a second tray when inverted; and removable support means for said surgical instruments and materials comprising a first insert board having means for removing said first insert board from said first tray and from said second tray of said cover, said first insert board comprising a planar element having a plurality of peg-receiving apertures and a plurality of pegs for removable placement in at least a portion of said peg-receiving apertures, said pegs being configured as hollow, tubular elements, each peg having an upper end and a bottom end, the bottom end terminating in a stop, said peg including a plurality of longitudinal slots extending an incremental distance from said stop and thereby forming legs in said peg, said peg including a circumferential ridge spaced from said stop and adapted to contact an upper surface of said first insert board when said peg is inserted upwardly through said peg-receiving aperture and said stop is engaged against a bottom surface of said first insert board, said slots extending above said upper surface and allowing the passage of sterilizing medium through said slots.

14. The container defined in claim 13 wherein said raised sidewalls include handles formed as outwardly extending projections from said sidewalls.

15. The container defined in claim 14 wherein said handles are formed as extensions of said marginal flange.

16. The container defined in claim 15 wherein said extensions include a bottom surface with a rim around the periphery of the bottom surface.

17. The container defined in claim 16 wherein said bottom surface includes an aperture for drainage.

18. The container defined in claim 13 wherein said cover includes outwardly extending projections which form handles for said cover.

19. The container defined in claim 18 wherein said handles correspond to said handles on said first tray and include at least one hole in each of said handles with said holes being in registry and adapted to receive a banding means for securing said container cover to said first tray.

20. The container defined in claim 13 wherein said first insert board comprises a planar element having a plurality of peg-receiving apertures, a plurality of hollow pegs for removable placement in at least a portion of said peg-receiving apertures and at least one retainer for releasably engaging the upper ends of said pegs and comprising a body extending between said pegs and having downwardly extending nipples dimensionally configured to be releasably engaged in said upper ends of said hollow pegs.

21. The container defined in claim 13, wherein a second removable insert board having at lease one depression formed therein for receiving a surgical instrument and a plurality of apertures.

22. The container defined in claim 13 wherein said container includes a plurality of vertical slots in said sidewalls and at least one divider means adapted to be releasably engaged in said vertical slots.

23. The container defined in claim 13 wherein said removable means means include a clip retainer comprising a retainer base and a plurality of vertical extensions fabricated from a resilient material and adapted to releasably engage said instruments between adjacent extensions, said extensions comprising clip fingers having enlarged upper ends.

* * * * *